(12) United States Patent
Friebe et al.

(10) Patent No.: US 8,231,668 B2
(45) Date of Patent: Jul. 31, 2012

(54) STENT FOR INTRODUCING INTO HUMAN BODY CAVITIES, IN PARTICULAR INTO BLOOD VESSELS

(76) Inventors: Michael Friebe, Recklinghausen (DE); Dietrich Baumgart, Essen (DE)

( * ) Notice: Subject to any disclaimer, the term of this patent is extended or adjusted under 35 U.S.C. 154(b) by 441 days.

(21) Appl. No.: 12/088,395

(22) PCT Filed: Oct. 2, 2006

(86) PCT No.: PCT/EP2006/009560
§ 371 (c)(1),
(2), (4) Date: May 20, 2008

(87) PCT Pub. No.: WO2007/039273
PCT Pub. Date: Apr. 12, 2007

(65) Prior Publication Data
US 2008/0288047 A1 Nov. 20, 2008

(30) Foreign Application Priority Data

Sep. 30, 2005 (DE) .......................... 10 2005 047 431
Oct. 29, 2005 (DE) .......................... 10 2005 052 226

(51) Int. Cl.
*A61F 2/06* (2006.01)
(52) U.S. Cl. ....................................... 623/1.15; 623/1.11
(58) Field of Classification Search ................. 606/108; 623/1.11, 1.12, 1.13, 1.18, 1.19, 1.2, 1.23, 623/1.22
See application file for complete search history.

(56) References Cited

U.S. PATENT DOCUMENTS
4,512,338 A 4/1985 Balko et al.
(Continued)

FOREIGN PATENT DOCUMENTS
DE 19703482 8/1998
(Continued)

OTHER PUBLICATIONS
International Search Report prepared by the European Patent Office on Dec. 22, 2006 for PCT/EP2006/009560; Applicant: Friebe et al.

*Primary Examiner* — Kathleen Sonnett
*Assistant Examiner* — Jonathan W Miles
(74) *Attorney, Agent, or Firm* — Jason H. Vick; Sheridan Ross, PC

(57) ABSTRACT

The invention relates to a stent (1) for introducing into human body cavities, in particular into blood vessels, comprising a proximal first end to be introduced (2) and a distal final end to be introduced (3), a sleeve-like stent body (4) made of biocompatible material, and at least one support wire (5) provided as a support body within the stent body (4), the support wire (5), when the stent is in the tensioned state, resting against the inside of the stent body (4) in the shape of a spiral and the stent body (4), when the stent is in a compressed state, being collapsed and expandable into a tensioned state. The proximal end of the support wire (5) in the region of the proximal first end to be introduced (2) is firmly attached to the stent body (4) and the distal end of the support wire, when the stent is in the compressed state, extending from the distal final end (3) of the stent body (4) to be introduced. The support wire (5) is a shape-retaining spring wire which in the compressed state is pre-tensioned at least in the region of the stent body (4) and is drawn into an elongated straight line and contracts in the longitudinal direction into the spiral shape at least in sections upon closing of the spring and expands radially in the form of a spiral in order to effect a radial expansion of the contracted stent body (4) until it reaches the tensioned state.

15 Claims, 2 Drawing Sheets

U.S. PATENT DOCUMENTS

Figure 1:
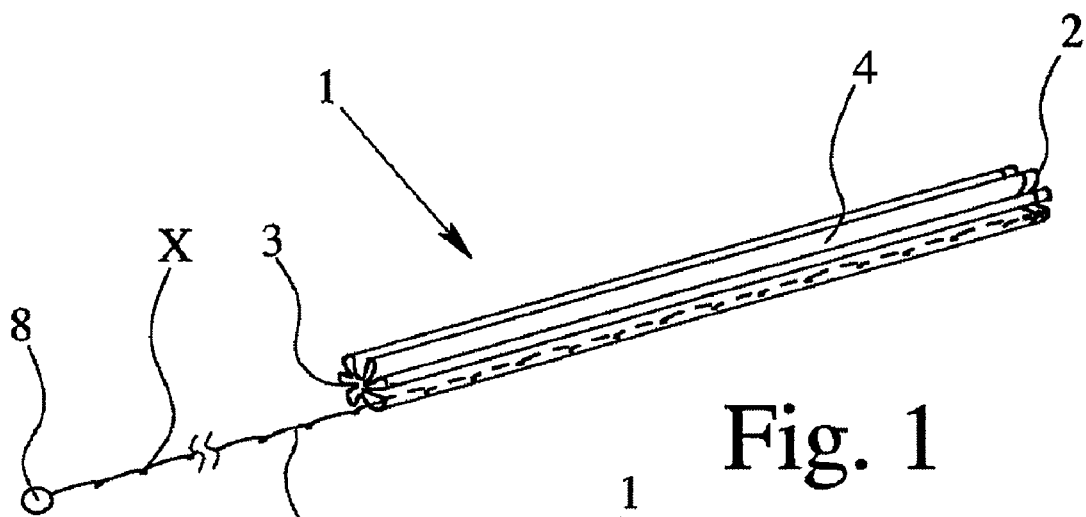

| | | | | |
|---|---|---|---|---|
| 4,787,900 | A | * | 11/1988 | Yannas ............................ 600/36 |
| 5,282,824 | A | * | 2/1994 | Gianturco .................... 623/1.13 |
| 5,683,449 | A | | 11/1997 | Marcade |
| 5,993,481 | A | * | 11/1999 | Marcade et al. ............. 623/1.35 |
| 6,022,369 | A | * | 2/2000 | Jacobsen et al. ............. 606/191 |
| 2004/0116996 | A1 | * | 6/2004 | Freitag ........................ 623/1.11 |

FOREIGN PATENT DOCUMENTS

| | | |
|---|---|---|
| DE | 199 56 249 | 6/2000 |
| DE | 101 18 944 | 10/2002 |
| DE | 202005001416 | 3/2005 |
| DE | 20 2005 001 416 | 8/2006 |
| EP | 0947180 | 10/1999 |
| WO | 90/04982 | 5/1990 |
| WO | WO 90/04982 | 5/1990 |
| WO | 93/21985 | 11/1993 |
| WO | 00/50116 | 8/2000 |
| WO | WO 01/41676 | 6/2001 |
| WO | 01/52770 | 7/2001 |
| WO | 2004/017868 | 3/2004 |

* cited by examiner

STENT FOR INTRODUCING INTO HUMAN BODY CAVITIES, IN PARTICULAR INTO BLOOD VESSELS

CROSS REFERENCE TO RELATED APPLICATIONS

This application is a national stage application under 35 U.S.C. 371 of PCT Application No. PCT/EP2006/009560 having an international filing date of Oct. 2, 2006, which designated the United States, which PCT application claimed the benefit of German Application Nos. 102005047431.4 filed Sep. 30, 2005 and 102005052226.2 filed Oct. 29, 2005, the entire disclosure of each of which is hereby incorporated herein by reference.

The invention relates to a stent with the features of the preamble of claim 1.

Stents of the aforementioned type are known from the prior art which are also referred to, in part, as prostheses. Such stents commonly serve to enlarge the cross-section of flow of the lumen of a (blood) vessel or to hold it permanently open. Moreover, stents are used in connection with the endovascular treatment of abdominal aortic aneurysms (AAA) to seal aneurysms (sacs).

Known stents are usually designed such that they resist the tendency of the vessel to narrow, so that the patency of the vessel is preserved. If the stent is provided for the sealing of an aneurysm, it must be additionally ensured that an invagination of the stent into the sac does not occur. Typical expandable stents generally have a tubular or sleeve-like shape and can be expanded from a folded-up, compressed state into a tensioned state. For the implantation, a compressed stent is usually placed in the desired implantation site with the aid of a catheter. There, the stent is pushed out of the catheter or pushed away from the catheter and expanded or unfolded. This can occur through self-expansion or by means of auxiliary devices. In so-called self-expanding stents, the stent is placed into the implantation site via an insertion catheter. Subsequently, the insertion catheter pushed over the stent or an external protective sleeve in the case of a stent pushed onto the insertion catheter is drawn off, which leads to an expansion of the stent into the tensioned position through the springing open of the support body. In stents that are not self-expanding, the expansion is usually achieved by means of a balloon provided on the inside of the stent into which a solution is generally introduced, so that the balloon expands and consequently tensions the stent. After a subsequent emptying of the balloon, it can be pulled out of the stent.

A stent of the type described at the outset is already known from DE 20 2005 001 416 which has at least one circumferential interrupted and/or uninterrupted spiral spring as a support frame. The spiral spring reinforces the elasticity of the stent in the longitudinal direction, which contributes to an easier introduction and removal of the stent into and out of a body cavity. Here, the stent body and the metallic support frame are formed in a non-expanding manner in the direction perpendicular to the longitudinal axis of the stent. It is disadvantageous that the known stent can sometimes be introduced into a body cavity with little lumen only with considerable effort or not at all. Moreover, with the known stent, an undesired shifting can occur in the body cavity in the tensioned state, which is also disadvantageous.

It is the object of the present invention to make available a stent of the type which can be introduced simply into a body cavity and carries out the function of supporting the surrounding tissue of the body cavity while eliminating the possibility of the occurrence of an undesired shifting of the stent in the body cavity in the tensioned state.

To achieve the objected named above, a stent with the features of claim 1 is proposed. First, it should be pointed out that the expression "proximal" has the meaning of "toward the heart," whereas the expression "distal" has the meaning of "away from the heart." The dimensional stability of the stent in the tensioned state is set in advance by the material of the stent body and the material of the support wire, as well as its spring force. In this manner, it is ensured that the stent resists the tendency of the vessel to narrow and that, in the case of the treatment of an abdominal aortic aneurysm, an invagination of the stent body into the aneurysm cannot occur.

The stent according to the invention offers a number of substantial advantages. In this connection, it is first important that the support wire is stretched or pretensioned in the longitudinal direction in the compressed state of the stent, which can also be referred to as the insertion state, so that, in the compressed state, the support wire is preferably designed to be substantially stretched out lengthwise until it is straight, optionally slightly coiled with a large coil spacing. As a result, in order to introduce the stent according to the invention into a body cavity, the support wire is drawn or pretensioned substantially in its entirety into a straight linear shape. As a result, it is possible to collapse the stent body to a very small diameter upon introduction of the stent into a body cavity, and the stent body can be wound very tightly around the stretched support wire, which simplifies introduction substantially. In order to keep the stent body in the collapsed state until the stent has reached the implantation site or the insertion region in the body, it can be pushed into an insertion catheter. Once the stent has reached the desired implantation site, the insertion catheter is withdrawn, which has as a consequence that the support wire springs into the spiral shape. Through the automatic winding of the support wire, an expansion of the collapsed stent body is effected up to the insertion volume, as a result of which the stent is held securely at the implantation site in the body cavity. Special tensioning means are not required in the stent according to the invention.

In the collapsed, compressed or insertion state of the stent, at least the distal end of the support wire is led out of the stent body at the distal final end to be introduced. Here, the support wire is stretched against its spring force. The stretched support wire can have a length prior to springing open which is many times the length of the support wire after springing open, particularly at least 1.5 times. Here, in the insertion state, the support wire is led out of the stent body at the distal final end to be introduced by at least a length which permits the springing open into the spiral shape and the formation of a support body of sufficient length in the stent body. Ultimately, remaining in the compressed state in the stent is only a support wire segment of such a length that is equal to or slightly larger than the length of the stent body. However, the region of the support wire led out of the stent body, which makes up the overwhelming majority of the length of the support wire, must not necessarily be tensioned. After all, it is only necessary to ensure that the support wire does not pull back into the stent in the compressed state of same and possibly at least partly expand it. In the tensioned state, the support body formed through the springing open of the support wire preferably extends in any case over the entire length of the stent body, thus ensuring a sufficient stability of the stent over its entire length.

In addition, it is also possible that the support wire not spring into the spiral shape over its entire length, but rather only in sections, so that there are spiral-shaped sections and substantially straight sections of the support wire after the springing open of the support wire or after the expansion of the stent body, which can in particular be arranged alternately next to each other in the longitudinal direction of the stent body. In the region of the straight sections of the support wire present after springing open, a facilitated access to the stent body is possible, for example in order to be able to connect the end or the beginning of another stent body to the stent body. However, a provision is preferably made that the support wire springs into a spiral shape over the entire length of the stent body.

Moreover, at least one reinforcement can be provided. The reinforcement should preferably extend on the inside of the stent body, i.e. between at least two layers of the stent body, in the longitudinal direction of the stent body. In principle, it is of course also possible that the reinforcement rest against the stent body from inside and be connected thereto, at least in areas. The reinforcement can be formed, for example, by an additional, linear support wire which contributes to the stabilizing of the stent body in the tensioned state. Here, the additional support wire can have the same length in the collapsed state of the stent body and in the expanded state of the stent body. In principle, it is of course also possible that an additional spring wire be provided as reinforcement which is preferably drawn into a linear shape stretched lengthwise in the collapsed state of the stent body and which contracts upon springing open, at least in sections, and contributes to a stiffening of the stent body in the tensioned state.

The support wire can be manufactured from a so-called shape-memory alloy, preferably from a nickel/titanium alloy, particularly from nitinol. The automatic expansion of the stent body is effected here through the spring force of the support wire, with the support wire springing out of an at least substantially stretched shape in the region of the stent body into a spiral shape. In principle, the support wire can of course also spring into other shapes which lead to the formation of a sufficiently stiff support frame. In the design of an AAA stent, the stent body consists of a biocompatible material, for example a PTFE membrane, particularly a GORE-TEX® membrane. A provision can be made here that the support wire is also guided within the membrane, i.e. between two membrane layers. Preferably, however, the support wire rests against the membrane.

The proximal end of the support wire is securely connected to the stent body in the region of the first end to be introduced. Consequently, the springing open of the support wire during the conversion from the insertion state into the tensioned state is facilitated, with the support wire coiling up in the direction of the first end to be introduced. To fasten the stent body to the support wire, the stent body can have at least one internal fastening section, preferably a fastening ring, for the support wire. In principle, however, it is also possible that the support wire be adhered to the stent body, and other positive or non-positive connections inherently known from the prior art can also be provided to fasten the support wire to the stent body.

In the tensioned state of the stent, the distal end of the support wire is arranged within the stent body and is preferably not fastened. Here, the support wire is preferably only securely connected to the stent body at the first end to be introduced. As a result, the handling of the stent is simplified, and it is not necessary to fix the support wire at its distal end after removal of the insertion catheter and the expansion of the stent body. The support wire is preferably pressed against the inside surface of the stent body and consequently fixed solely due to its spring force.

For simplified guiding of the support wire on the inside of the stent body, a plurality of guide sections can be provided on the inside wall of the stent body. The guide sections can be loops, for example, in which the support wire is guided such that it can be moved freely in the axial direction. In this regard, it is essential that there be no hindrance to the springing open of the support wire into the spiral shape as a result of the guide sections, which would have an incomplete expansion of the collapsed stent body as a consequence.

In order for the expanded stent to resist the tendency of the vessel to narrow in all cases or to prevent an invagination into a sac (aneurysm), the spiral-shaped support body formed from the support wire in the tensioned state by springing open preferably has a coil spacing of between 0.2 cm to 2 cm, particularly between 0.5 cm to 1 cm.

In the insertion state, the stent body can have a length of 5 cm to 30 cm, preferably of 8 cm to 15 cm. Here, as needed, the invention permits the stent to have a length in the insertion state which facilitates the use of the stent for the bridging of vascular sections of different lengths. Prior to or during an operation and depending on the required length of the stent, the stent body can be shortened as needed. Accordingly, the length of the support wire is also shortened accordingly, and the non-shortened support wire should have a sufficient length which facilitates the use of the stent for the bridging of vascular sections of different lengths. In the stretched state of the support wire, the coil diameter can preferably be less than 0.5 cm, particularly less than 0.2 cm.

The support wire can be designed to be spring-opening in an Archimedean shape or in the shape or a logarithmic spiral. Accordingly, in the tensioned state, the stent body has a cylindrical shape or a cone shape, which facilitates use in various vessels of the body.

Preferably, in the tensioned state as well, the support wire is radially pretensioned in the spiral shape such that spring forces act in the support wire in the radial direction even after the springing open in the stent body, and these spring forces have the consequence that the support wire rests closely against the stent body, stabilized same over the entire length and also resulting in a secure position of the stent in the blood vessel. Here, the support body does not assume its greatest possible diameter based on the pretension of the support wire on the inside of the stent body. The volume of the support body is limited by the maximum insertion volume of the stent body to a relatively small diameter. In this manner, it is ensured that the support wire rests on the inside surface of the stent body and an optimal support effect is ensured by the support body.

In the tensioned state, the stent body can have an outward taper at the first end to be introduced and/or at the final end to be introduced. It is advantageous here if the stent has a greater diameter at its proximal end than in the other regions in order to ensure a sufficient seal and a secure abutment of the stent body against the body cavity in this region. This has as a consequence that the stent, after the expansion of the stent body to the insertion volume, is fixed at the implantation site. In this connection, the support wire can also have at least two regions which spring open into different spiral shapes. Through springing open of the support wire into corresponding spiral shapes, an expansion of the stent body in a middle region of the stent into a cylindrical shape and at the ends of the stent into a tapered shape can be brought about.

The support wire can have at least one predetermined breaking point which makes it possible to shorten the length of the support wire in the body cavity as well, depending on the required length of the stent in the tensioned state. The required length of the support wire is predetermined by the length of the stent body in the tensioned state, and the support body should have a length after springing open of the support wire which preferably corresponds to the length of the stent body. Here, the support wire can be shortened prior to introduction or also endoscopically after the implantation site has been reached.

To be able to slowly move the support wire for springing open into the spiral shape such that a defined expansion is ensured, the support wire preferably has a gripping section at its distal end for a gripper device. The gripping section is preferably a loop or a knot.

The stent body can have, on its outside, projections and/or a membrane with high porosity and/or high surface roughness at least of the outer surface. As a result, the growth of cells on the stent body is supported in the tensioned state and the position of the stent is further fixed in the body cavity.

In addition, a substantial advantage of the stent according to the invention lies in the fact that the stent body can be opened at one area in a simple manner in the implanted state of the stent in order to push a stent body of an adjacent additional stent with a smaller insertion volume into the opening and to bridge a vascular junction in the body. Producing such a junction over a stent is possible by very simple means, since the support wire is connected to the stent body only at the proximal end but is otherwise not connected. In this manner, the stent body can be cut into without further ado and another stent can be placed into the incision and fixed.

Figure 2:
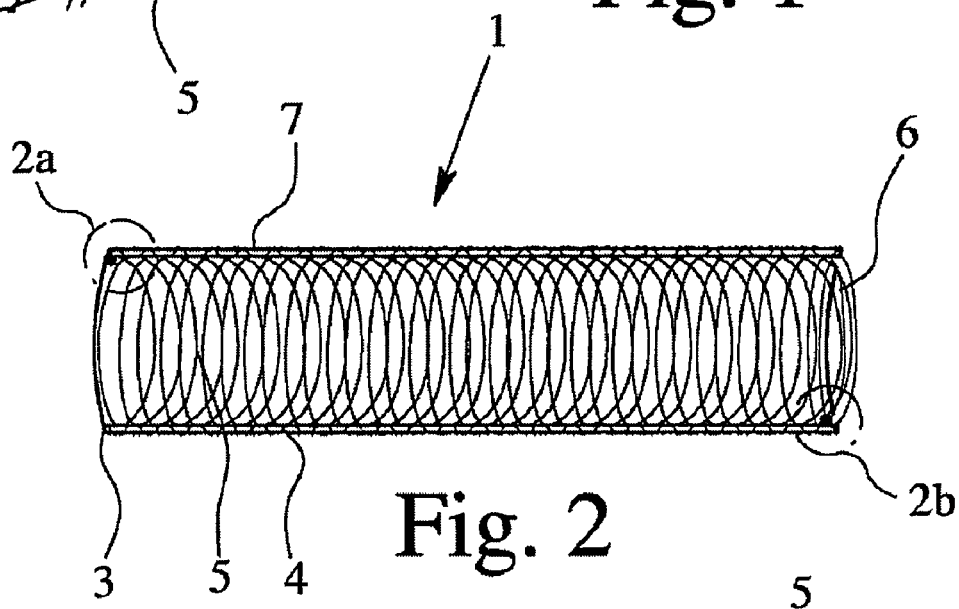
Figure 3:
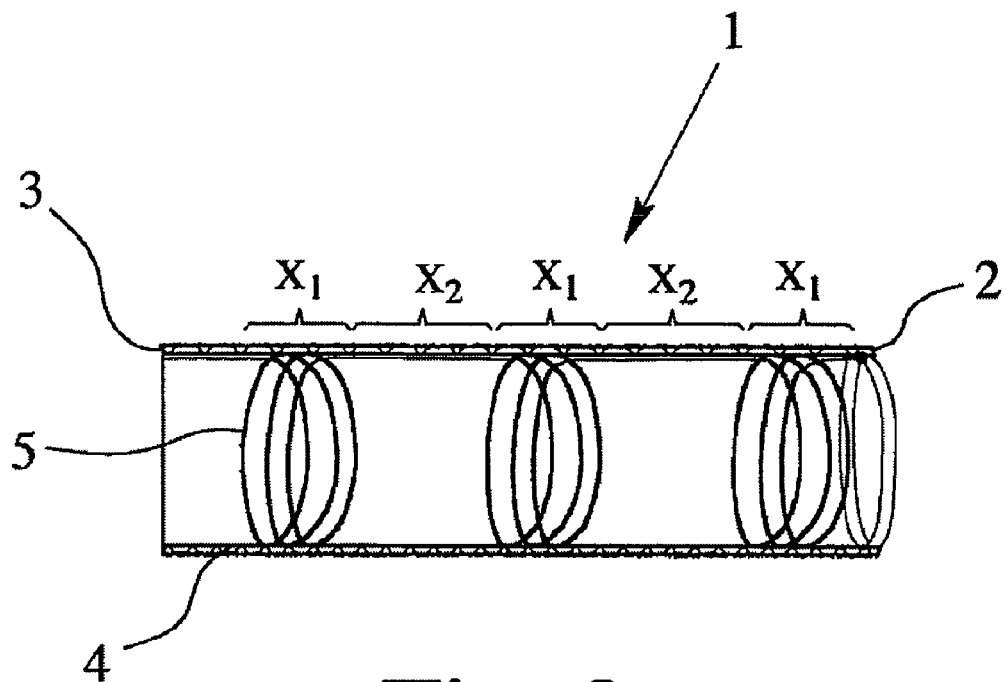
Figure 4:
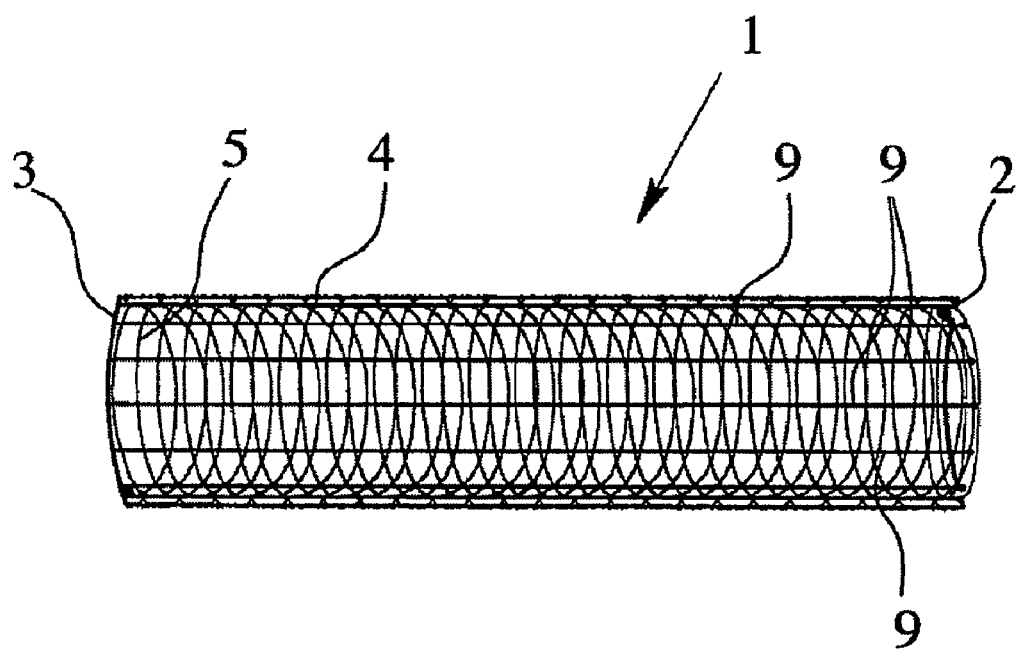

Specifically, there are a number of possibilities for designing and modifying the stent according to the invention, in which regard reference is made, on the one hand, to the dependent patent claims and, on the other hand, to the following detailed description of a preferred sample embodiment of the invention with reference to the drawing. In the drawing, FIG. 1 shows a schematic view of a compressed stent according to the invention, FIG. 2 shows a view of the stent from FIG. 1 in the tensioned state, FIG. 3 shows a schematic view of another embodiment of a stent in the tensioned state, and FIG. 4 shows a schematic view of a third embodiment of a stent in the tensioned state.

Shown in FIG. 1 is a stent 1 for introduction into human body cavities and, particularly, into blood vessels, with a proximal first end to be introduced 2 and a distal final end to be introduced 3 in an insertion state. The stent 1 has a schematically depicted collapsed or folded stent body 4 and a support wire 5 provided on the inside of the stent body 4.

In the compressed, folded insertion state which is depicted in FIG. 1, the stent body 4 has a relatively small insertion volume, with the stent body 4 being compressed in the radial direction. In order to maintain the stent 1 in the insertion state, an insertion catheter or a so-called insertion gate (not depicted) is provided into which the stent 1 is pushed for introduction into the body. The stent 1 is pushed into the vessel and preferably positioned at the desired position under radiological control (image intensifier). In order to convert the stent 1 into a tensioned state, the insertion catheter is withdrawn, while the stent 1 remains at the implantation site, which leads to a springing open of the support wire 5 and to an expansion or unfolding of the stent body 4 due to the pretension of the support wire 5. Here, the tensioning of the stent body 4 can be performed defined by the support wire 5, with the distal end being moved slowly by use of an appropriate tool in the direction of the stent body. In principle, the invention permits execution of a final anchoring of the stent through balloon dilation.

If the stent 1 is pushed into the body inside the insertion catheter, then the insertion catheter prevents the tensioning of the stent body 4. However, it is also possible in principle that the stent body 4 be pushed up onto a catheter, with the tensioning of the stent body 4 being prevented during introduction into the body by an external protective sleeve or the like. To convert the stent 1 to a tensioned state, the protective sleeve is then first withdrawn, while the stent 1 remains at the implantation site, so that the opening of the stent body 4 occurs. After the opening of the stent body 4, the catheter can then be withdrawn as well. For this, tools inherently known from the prior art can be used.

Moreover, it is also possible that the support wire 5 as such be prevented from springing open during the introduction of the stent 1 into the body, with an arrangement of the protective sleeve between the external stent body 4 and the internal support wire 5 being possible. In addition, another external protective sleeve can be provided for the stent body 4 to maintain the stent body 4 in a folded state during introduction of the stent 1 into the body.

In the tensioned state illustrated in FIG. 2, the stent 1 has an enlarged insertion volume, and the support wire 5 rests on the inside surface of the stent body 4 in a spiral shape.

By stretching the support wire 5 in the longitudinal direction against the spring force, and through the reduction in the diameter of the spiral-shaped support body brought about therewith, it is possible in the insertion state to collapse or compress the stent body 4 to a very small insertion diameter, which simplifies the insertion process substantially.

In the illustrated embodiment of the invention, a provision is made that the support wire 5 is fastened at its proximal end in the region of the proximal first end to be introduced 2 of the stent 1 to the stent body 4 and is led out with its distal end in the insertion state from the stent body 4 at the distal final end to be introduced 3 of the stent 1. This is shown in FIG. 1.

Figure 2A:
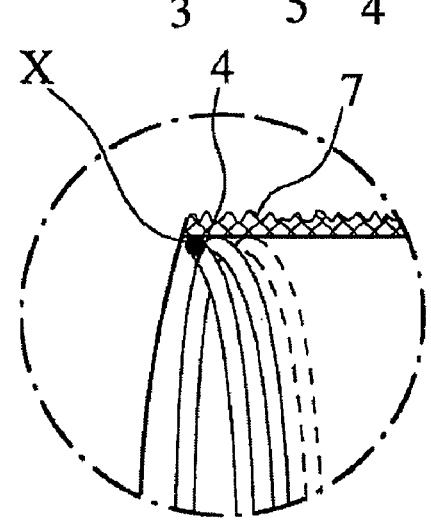

In the tensioned state, a provision is preferably made that the support wire 5 is arranged and not fastened on the inside of the stent body 4. For this purpose, a provision is preferably made to separate the support wire 5 at position X prior to the conversion of the stent 1 into the tensioned state, as a result of which it is ensured that the distal end of the support wire 5 is arranged inside the expanded stent body 4 after springing open. This is shown in FIG. 2a.

Figure 2B:
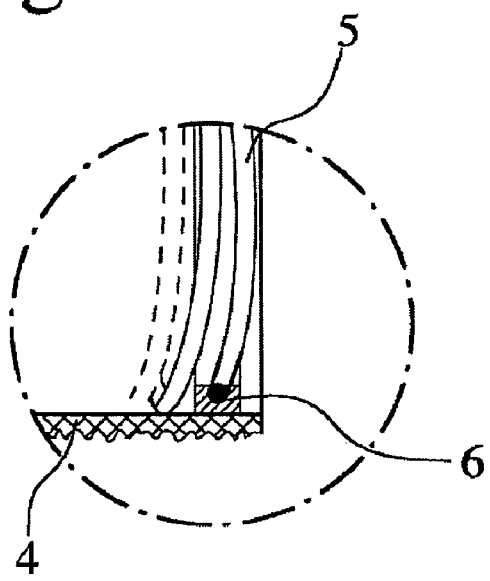

The support wire 5 is securely connected at its proximal end in the region of the proximal first end to be introduced 2 of the stent 1 to the stent body 4 via a fastening ring 6. This is shown in FIG. 2b. In addition, a provision can be made that, in the region of the proximal first end to be introduced 2 of the stent 1, the spiral-shaped support body formed from the support wire 5 by springing open has a smaller coil spacing in the tensioned state than in the middle region or in the region of the distal final end to be introduced 3 of the stent 1, and/or that the support wire 5 springs into the spiral shape in a zigzag or wavy manner at its proximal end. In this manner, a high pressing force on the proximal first end to be introduced 2 can be ensured.

The support wire 5 is embodied as a shape-retentive spring wire made of a shape-memory alloy and is pretensioned in the insertion state at least in the region of the stent body 4 and is stretched lengthwise at least substantially. Preferably, in this connection, a detachable limit stop is provided to fix the support wire 5 in the state in which it is stretched out and led out of the stent body 4 and maintains the support wire in the stretched-out position.

In comparing FIGS. 1 and 2, it becomes clear that the support wire 5 is stretched in the insertion state substantially directly against the spring force and has coils with at most a large coil spacing. In the tensioned state, the support body formed from the support wire 5 has a length on the inside of the stent body 4 which corresponds substantially to the length of the stent body 4.

In FIG. 2, it is further shown that the stent body 4 has on the outside projections 7 and/or a membrane with a high porosity and/or high surface roughness at least of the outer surface. As a result, the growth of cells after the insertion of the stent 1 into a body cavity is supported, which has as a consequence that the stent 1 is fixed in its position in the body.

Moreover, it follows from FIG. 1 that the support wire 5 can have a gripping section 8 at its distal end in the insertion state. The gripping section 8 makes it possible to hold the support wire 5 with an appropriate tool during introduction and upon shortening.

In FIGS. 3 and 4, other possible embodiments of a stent 1 are shown, with the support wire 5 not being spring-opened into a spiral shape over the entire length of the stent body 4 in FIG. 3. In the tensioned state of the stent body 4, the support wire 5 therefore has sections $X_1$ on the one hand over the length of which the support wire 5 is spring-opened into a spiral shape. Over the length of other sections $X_2$, the support wire 5 has, on the other hand, a substantially stretched-out linear shape. The sections $X_1$ and the other sections $X_2$ are arranged alternately next to each other. The stretched-out shape of the support wire 5 in the area of the other sections $X_2$ simplifies the opening of the stent body 4 in this region and the connection of another stent (not depicted) to the stent body 4, with the stent body of the other stent being connected to the stent body 4.

According to FIG. 4, reinforcements 9 are provided which have a straight linear shape and extend in the longitudinal direction of the stent 1. The reinforcements 9 are provided to increase the rigidity of the stent 1 in the tensioned state of the stent body 4. The reinforcements 9 can be connected to the stent body 4 at least in sections or even run on the inside of the stent body 4. Depending on the selected application site of the stent 1 in the body, the reinforcements 9 can be embodied to be more or less flexible. The reinforcements 9 are preferably embodied as non-spring-expanding wires. However, it is also possible in principle that the reinforcements 9 be spring wires which extend, for example, in a zigzag manner in the tensioned state and that they be drawn into a stretched-out straight linear shape in the collapsed state and are led out of the distal final end to be introduced 3 of the stent body 4.

The invention claimed is:

1. Stent for introducing into human body cavities with a proximal first end to be introduced and a distal final end to be introduced, with a sleeve-like stent body made of biocompatible material and with at least one support wire provided on the inside of the stent body, wherein the support wire rests in a spiral shape on the inside in a tensioned state of the stent, wherein the stent body is collapsed in a compressed insertion state of the stent and is expandable into the tensioned state, wherein the support wire is securely connected at its proximal end in the region of the proximal first end to be introduced to the stent body and is led, with its distal end in the compressed insertion state, out of the distal final end to be introduced of the stent body, wherein the support wire is embodied as a shape-retentive spring wire which is pretensioned in the compressed insertion state at least in the region of the stent body and is drawn into a stretched-out straight linear shape over an entire length of the stent body and which contracts in the longitudinal direction upon springing open at least in sections into the spiral shape and expands radially in a spiral shape in order to effect a radial expansion of the collapsed stent body until the tensioned state is reached, wherein a support wire section of the support wire which extends inside the stent body from the distal final end to be introduced to the proximal first end to be introduced of the stent body has substantially the same length as the stent body in the compressed insertion state of the stent, with the support wire fastened to an interior fastening ring provided at the proximal first end to be introduced of the stent body and with the support wire freely movable in the axial direction guided in the interior of the stent body, wherein a plurality of guide sections are provided in the inner surface of the stent body to guide the support wire, wherein the guide sections are loops in which the support wire is guided such that it can be moved freely in the axial direction, wherein a reinforcement is provided which extends on the inside of the stent body in the longitudinal direction of the stent body, wherein the reinforcement is a non-spring-expanding wire and wherein in the stretched state of the support wire, the coil diameter is less than 0.5 cm, or less than 0.2 cm.

2. Stent as set forth in claim 1, wherein the support wire springs into the spiral shape over the entire length of the stent body.

3. Stent as set forth in claim 1, wherein, in the tensioned state, the distal end of the support wire is arranged on the inside of the stent body and is not fastened.

4. Stent as set forth in claim 1, wherein, in the tensioned state, the support wire is securely connected to the stent body only at the proximal first end to be introduced.

5. Stent as set forth in claim 1, wherein, in the tensioned state, the spiral-shaped support body formed from the support wire in the tensioned state by springing open has a coil spacing of between 0.2 cm to 2 cm.

6. Stent as set forth in claim 1, wherein, in the tensioned state, the spiral-shaped support body formed form the support wire in the tensioned state by springing open has a coil spacing of between 0.5 cm to 1 cm.

7. Stent as set forth in claim 1, wherein, in the compressed insertion state, the stent body has length of 5 cm to 30 cm.

8. Stent as set forth in claim 1, wherein, in the compressed insertion state, the stent body has a length of 8 cm to 15 cm.

9. Stent as set forth in claim 1, wherein the support wire is embodied to spring open into the shape of an Archimedean or a logarithmic spiral.

10. Stent as set forth in claim 1, wherein the support wire is pretensioned radially into the spiral shape in the tensioned state after springing open.

11. Stent as set forth in claim 1, wherein the support wire has at the distal end a gripping section for a gripper device.

12. Stent as set forth in claim 1, wherein the stent body has projections on the outside.

13. Stent as set forth in claim 1, wherein the stent body has a membrane with at least one of high porosity and high surface roughness at least on the external surface.

14. Stent for introducing into human body cavities with a proximal first end to be introduced and a distal final end to be introduced, with a sleeve-like stent body made of biocompatible material and with at least one support wire provided on the inside of the stent body, wherein the support wire rests in a spiral shape on the inside in a tensioned state of the stent, wherein the stent body is collapsed in a compressed insertion state of the stent and is expandable into the tensioned state, wherein the support wire is securely connected at its proximal end in the region of the proximal first end to be introduced to the stent body and is led, with its distal end in the compressed insertion state, out of the distal final end to be introduced of the stent body, wherein the support wire is embodied as a shape-retentive spring wire which is pretensioned in the compressed insertion state at least in the region of the stent body and is drawn into a stretched-out straight linear shape over an entire length of the stent body and which contracts in the longitudinal direction upon springing open at least in sections into the spiral shape and expands radially in a spiral shape in order to effect a radial expansion of the collapsed stent body until the tensioned state is reached, wherein the support wire section of the support wire which extends inside the stent body from the distal final end to be introduced to the proximal first end to be introduced of the stent body has substantially the same length as the stent body in the compressed insertion state of the stent, with the support wire fastened to an interior fastening ring provided at the proximal first end to be introduced of the stent body and with the support wire freely movable in the axial direction guided in the interior of the stent body, wherein at least one reinforcement is provided which extends on the inside of the stent body in the longitudinal direction of the stent body, wherein the at least one reinforcement is a non-spring-expanding wire, and wherein in the stretched state of the support wire, the coil diameter is less than 0.5 cm, or less than 0.2 cm.

15. Stent for introducing into human body cavities with a proximal first end to be introduced and a distal final end to be introduced, with a sleeve-like stent body made of biocompatible material and with at least one support wire provided on the inside of the stent body, wherein the support wire rests on the inside of the stent body in combination of spiral shaped portions and substantially stretched out linear portions when in a tensioned state of the stent, the spiral shaped portions and substantially stretched out linear portions alternating along a length of the stent body, wherein the stretched out linear portions extend parallel to the longitudinal axis of the stent body and the spiral shaped portions extend transverse to the longitudinal axis of the stent body, wherein the stent body is collapsed in a compressed insertion state of the stent and is expandable into the tensioned state, wherein the support wire is securely connected at its proximal end in the region of the proximal first end to be introduced to the sent body and is led, with its distal end in the compressed insertion state, out of the distal final end to be introduced of the stent body, wherein the support wire is embodied as a shape-retentive spring wire which is pretensioned in the compressed insertion state at least in the region of the sent body and is drawn into a stretched-out straight linear shape and which contracts in the longitudinal direction upon springing open at least in sections into the spiral shape and expands radially in a spiral shape in order to effect a radial expansion of the collapsed stent body until the tensioned state is reached, wherein a support wire section of the support wire which extends inside the stent body from the distal final end to be introduced to the proximal first end to be introduced of the stent body has substantially the same length as the stent body in the compressed insertion state of the stent, with the support wire fastened to an interior fastening ring provided at the proximal first end to be introduced of the stent body and with the support wire freely movable in the axial direction guided in the interior of the stent body, wherein the support wire does not spring into the spiral shape over its entire length, but rather only in sections, so that there are spiral-shaped sections and substantially straight sections of the support wire on the inside of the stent body after the springing open of the support wire, and wherein a reinforcement is provided which extends on the inside of the stent body in the longitudinal direction of the stent body, wherein the reinforcement is a non-spring-expanding wire.

* * * * *